(12) United States Patent
Alitalo et al.

(10) Patent No.: US 11,512,272 B2
(45) Date of Patent: Nov. 29, 2022

(54) SOLID STATE FERMENTATION REACTOR EQUIPPED WITH ACTIVE SUPPORT MATERIAL

(71) Applicant: Qvidja Kraft AB, Lielahti TL (FI)

(72) Inventors: Anni Alitalo, Espoo (FI); Marko Niskanen, Vantaa (FI); Erkki Aura, Tammela (FI)

(73) Assignee: Q POWER OY, Lielahti TL (FI)

( * ) Notice: Subject to any disclaimer, the term of this patent is extended or adjusted under 35 U.S.C. 154(b) by 859 days.

(21) Appl. No.: 16/312,238

(22) PCT Filed: Jun. 21, 2017

(86) PCT No.: PCT/FI2017/050466
§ 371 (c)(1),
(2) Date: Dec. 20, 2018

(87) PCT Pub. No.: WO2017/220862
PCT Pub. Date: Dec. 28, 2017

(65) Prior Publication Data
US 2019/0241848 A1     Aug. 8, 2019

(30) Foreign Application Priority Data

Jun. 23, 2016 (FI) .................................. 20165527

(51) Int. Cl.
*C12M 1/107* (2006.01)
*C12N 11/14* (2006.01)
(Continued)

(52) U.S. Cl.
CPC .............. *C12M 21/04* (2013.01); *C12M 1/04* (2013.01); *C12M 1/107* (2013.01); *C12M 1/16* (2013.01);
(Continued)

(58) Field of Classification Search
CPC ........ C12M 21/04; C12M 1/04; C12M 1/107; C12M 1/16; C12M 25/18; C12N 1/20;
(Continued)

(56) References Cited

U.S. PATENT DOCUMENTS

| 4,921,799 A * | 5/1990 | Kitaura ..................... C12P 7/40 |
| | | 435/167 |
| 6,524,843 B1 * | 2/2003 | Blais ...................... B01D 53/84 |
| | | 435/266 |

(Continued)

FOREIGN PATENT DOCUMENTS

| CN | 101903512 A | 12/2010 |
| CN | 101918530 A | 12/2010 |

(Continued)

OTHER PUBLICATIONS

First Office Action received for Chinese Patent Application Serial No. 201780044991.5 dated Aug. 2, 2021, 15 pages. (Including English Translation).

(Continued)

*Primary Examiner* — William H. Beisner
*Assistant Examiner* — Danielle B Henkel
(74) *Attorney, Agent, or Firm* — FisherBroyles, LLP (57) ABSTRACT

An active solid state fermentation bioreactor for producing gases, liquid(s) or solids from gaseous or gaseous and liquid starting materials and a fermentation process using the reactor are disclosed, The bioreactor includes three major phases; a solid phase including the porous solid support, a liquid phase comprising liquid, and a gaseous phase. The solid phase includes a porous solid support, in which at least 20% of the pore volumes have a size resulting in a liquid suction of about 0.01 to about 0.1 bars if these pores are filled with liquid, the porous solid support is inoculated with desired micro-organisms, the volume of the gaseous phase is (Continued)

20% to 60% of the volume of the bioreactor, and the liquid phase is at least 20% of the reactor volume, The unsaturated capillary conductivity of filling/packing solid material of the bioreactor is at least 0.1 cm/ h. The solid state fermentation bioreactor enables a large gas-liquid interface, in which the filling material has a good capillary conductivity despite the unsaturated state.

14 Claims, 4 Drawing Sheets

(51) Int. Cl.
    *C12M 1/04*     (2006.01)
    *C12P 1/04*     (2006.01)
    *C12N 1/20*     (2006.01)
    *C12P 7/02*     (2006.01)
    *C12P 7/40*     (2006.01)
    *C12M 1/16*     (2006.01)
    *C12M 1/12*     (2006.01)
    *C12P 5/02*     (2006.01)

(52) U.S. Cl.
    CPC ............... *C12M 25/18* (2013.01); *C12N 1/20* (2013.01); *C12N 11/14* (2013.01); *C12P 1/04* (2013.01); *C12P 5/02* (2013.01); *C12P 7/02* (2013.01); *C12P 7/40* (2013.01)

(58) Field of Classification Search
    CPC .... C12N 11/14; C12P 1/04; C12P 5/02; C12P 7/40; C12P 7/02
    See application file for complete search history.

(56) References Cited

U.S. PATENT DOCUMENTS

| | | | |
|---|---|---|---|
| 6,620,614 B1* | 9/2003 | Luth | C12M 21/16 435/291.3 |
| 2004/0154982 A1* | 8/2004 | Irani | C12M 23/36 210/603 |
| 2005/0059141 A1* | 3/2005 | Wismar | C12M 41/24 435/289.1 |
| 2007/0218540 A1* | 9/2007 | Guiot | C12M 23/36 435/262.5 |
| 2009/0305391 A1* | 12/2009 | Parent | B01D 53/85 435/266 |
| 2010/0233775 A1* | 9/2010 | Schroder | C12M 41/00 435/167 |
| 2011/0281333 A1 | 11/2011 | Brown et al. | |
| 2012/0028321 A1* | 2/2012 | Criddle | C12P 7/625 435/146 |
| 2015/0099286 A1* | 4/2015 | Alitalo | C12P 5/023 435/167 |

FOREIGN PATENT DOCUMENTS

| | | |
|---|---|---|
| CN | 102559783 A | 7/2012 |
| CN | 104395476 A | 3/2015 |
| EP | 0603989 A2 | 6/1994 |
| WO | 0001803 A1 | 1/2000 |
| WO | 2013167806 A1 | 11/2013 |
| WO | 2016/097478 A1 | 6/2016 |

OTHER PUBLICATIONS

Extended European Search Report received for EP Patent Application Serial No. 17814822.7 dated Feb. 4, 2020, 6 pages.
Notice of Reasons for Refusal received for Japanese Patent Application Serial No. 2018-567148 dated Nov. 19, 2019, 9 pages. (Including English Translation).
Decision of Refusal received for Japanese Patent Application Serial No. 2018-567148 dated Jul. 14, 2020, 7 pages. (Including English Translation).
Decision to Grant a Patent received for Japanese Patent Application Serial No. 2018-567148 dated Dec. 22, 2020, 5 pages. (Including English Translation).
International Search Report for PCT/FI2017/050466 dated Oct. 11, 2017.
Written Opinion for PCT/FI2017/050466 dated Oct. 11, 2017.
International Preliminary Report on Patentability for PCT/FI2017/050466 dated May 28, 2018.
Search Report for Finnish Application No. 20165527 dated Jan. 16, 2017.
Anni Alitalo et al., "Biocatalytic methanation of hydrogen and carbon dioxide in a fixed bed bioreactor", Bioresource Technology 2015, vol. 196, Aug. 14, 2015, pp. 600-605.
Edward J. Wolfrum et al. "Bioreactor Design Studies for a Novel Hydrogen-Producing Bacterium", Proceedings of the 2001 DOE Hydrogen Program Review, Apr. 17, 2001, pp. 11-22.
Elizabeth C. Bugante et al., "Methane Production from Hydrogen and Carbon Dioxide and Monoxide in a Column Bioreactor of Thermophilic Methanogens by Gas Recirculation", Journal of Fermentation and Bioengineering 1989, vol. 67, No. 6, Apr. 1, 1989, pp. 419-421.
Communication of a notice of opposition received for EP Patent Application Serial No. 17814822.7 dated Mar. 7, 2022, 41 pages.
Sciencedirect, "Vermiculite—An Overview", URL: https://www.sciencedirect.com/topics/agricultural-and-biological-sciences/vermiculite. Biogeochemistry of Trace Elements in the Rhizosphere, 2005, pp. 1-9.
Sciencedirect, "Perlite—An Overview", URL: https://www.sciencedirect.com/topics/agricultural-and-biological-sciences/perlite. Advances in Botanical Research, 2011, pp. 1-20.
"What is Hydraulic Conductivity", URL: https://www.preene.com/blog/2014/07/what-is-hydraulic-conductivity, Blog, Jul. 8, 2014, pp. 1-6.
Schmidt et al., "Effects of the reduction of the hydraulic retention time to 1.5 days at constant organic loading in CSTR, ASBR, and fixed-bed reactors—Performance and methanogenic community composition", ScienceDirect, Biomass and Bioenergy, vol. 69, 2014, pp. 241-248.

* cited by examiner

SOLID STATE FERMENTATION REACTOR EQUIPPED WITH ACTIVE SUPPORT MATERIAL

CROSS-REFERENCE TO RELATED APPLICATIONS

This application is a U.S. National Stage Application of International Patent Application No. PCT/FI2017/050466, filed Jun. 21, 2017, which claims benefit of Finnish Patent Application No. 20165527, filed Jun. 23, 2016, both of which are incorporated by reference herein in their entirety.

BACKGROUND

Field

The present invention relates to an active solid state fermentation bioreactor for producing gases, liquid(s) or solids from gaseous or gaseous and liquid starting materials and to a fermentation process using such reactor.

Description of the Related Art

Solid-state fermentation has emerged as a potential technology for the production of microbial products such as feed, fuel, food, industrial chemicals and pharmaceutical products. Solid state fermentation processes provide several advantages over liquid fermentation processes. Solid state fermentation occurs in solid-state reactors which may naturally provide a large gas-phase and at the same time form a continuous liquid filled pore system. Furthermore, remarkably dense microbial growth on the moist solid particles may be achieved on a sufficient surface area resulting in high fermentation efficiency. The solid-state approach is particularly suitable for large-scale fermentation processes and bioreactors in cases where the aim is to build low-cost bioreactors with low maintenance costs due to low unit prices of the end product.

There are some disadvantages associated with the solid-state fermentation, too. For instance, owing to varying physical and chemical environmental conditions, the microbial growth and its efficacy may be unevenly distributed over the solid support particles in the reactor. Since the solid-state bioreactors cannot be homogenized by stirring, the availability of nutrients to the microorganisms may be uneven and it may be difficult to provide pH control. Furthermore, aeration or transfer of gaseous substances between different parts of the bioreactor may be limited. This may, for instance, be due to a blockade of the inter-particle space by condensing water, or water produced in the bioreaction. On the other hand, in cases where the bioreaction does not produce water, the solid particles may desiccate owing to gravity or gas flows, reducing the capillary conductivity of the liquid products in the reactor and simultaneously lowering the fermentation capacity of the microorganisms.

The existing solid state fermenter designs are not particularly advanced. In particular solid state fermentation lacks the sophisticated mechanisms to monitor several process parameters in a bioreactor such as pH, temperature, aeration, and oxygen transfer and moisture etc.

An important problem in the solid state bioreactors is how to maintain a high gas volume and a liquid capillary conductivity at the same time. A large gas volume/space is required for the residence time of the gases to be long enough to react in a reactor. A large interface area between the gas and liquid is necessary in order to obtain a high gas to liquid transfer efficiency.

Once the gas space/volume increases the interface between a liquid and a gas increases due to the fact that the interface will always go into smaller pores. However, for maintaining appropriate nutrient content and pH-value for microbes, a continuous liquid circulation is needed, when the reactors filling material is passive. Passive filling material is not able to control the nutrient contents and the pH-value of liquid in the reactor.

One problem in the solid state fermentation bioreactors is that the higher the gas space of the reactor is, the smaller is the capillary conductivity of the liquid. If the starting material or the product is liquid, low capillary conductivity causes filling of the pores with liquid and decreases gas transfer through the gas—liquid interface.

SUMMARY

An object of the present invention to provide an apparatus for solid state fermentation and a method for solid state fermentation so as to solve the above problems, especially when the bioreaction involves gaseous starting materials and liquid, gaseous or solid reaction products or their mixture. The objects of the invention are achieved by an arrangement and a method which are characterized by what is stated in the independent claims.

The present invention relates to a bioreactor comprising a gas or gas and liquid distribution system and a gas, liquid or solids collection system, wherein the bioreactor comprises a solid phase, a liquid phase and a gaseous phase, the solid phase comprises a porous solid support in which at least 20% of the pore volumes have a size resulting in a liquid suction of about 0.01 to about 0.1 bars if these pores are filled with liquid; the porous solid support is inoculated with desired micro-organisms; the volume of the gaseous phase is 20% to 60% of the volume of the bioreactor and the liquid phase is at least 20% of the reactor volume. The unsaturated capillary conductivity of filling/packing solid material of the bioreactor is at least 0.1 cm/h and said solid support has a cationic exchange capacity of at least 0.1 mmol/g, anion exchange capacity of at least 0.01 mmol/g, and a specific surface area of at least 5 $m^2$/g.

The present invention relates also to a process for generating liquid product(s) by solid state fermentation, comprising the steps of a) providing a bioreactor according to the present invention, b) feeding gas or gas and liquids into the reactor, c) anaerobically or aerobically bioconverting said gas(es) or gases and liquids into gaseous, liquids or solid products, and d) collecting said products from the bioreactor.

Specific embodiments of the invention are set forth in dependent claims. Other aspects, details, embodiments and advantages of the present invention will become apparent from the following drawings, detailed description and examples.

The present invention avoids the problems of nutrient content control and the pH-value control by using active filling materials instead of the passive. This enables partial empting of liquid from the filling material pores thus enabling a large area between gas and liquid. The used pore size distribution of the filling material determines the capillary conductivity of unsaturated material.

The present invention provides a solid state fermentation bioreactor which enables a large gas-liquid interface and in which the filling material has a good capillary conductivity despite the unsaturated state.

BRIEF DESCRIPTION OF THE DRAWINGS

In the following the invention will be described in greater detail by means of preferred embodiments with reference to the attached drawings, in which

FIG. 4 illustrates a liquid product exiting the solid state bioreactor by gravitation. The figure shows gas components ($CH_4$, $CO_2$) in the outlet gas (vol %), hydrogen supply, hydrogen conversion rate (%) and power (productivity) during a 45 hours study period (conducting biocatalytic methanation of carbon dioxide and hydrogen).

DETAILED DESCRIPTION

The present invention relates to a bioreactor and a solid state fermentation (SSF) process, wherein gas(es) or gas(es) and liquid(s) are converted to gas(es) or liquid(s) or solid(s) by desired micro-organisms grown on a porous solid support. The bioreactor according to the present invention comprises three major phases; a solid phase comprising the porous solid support, a liquid phase comprising liquid and a gaseous phase.

In order to achieve a long enough reaction time for starting materials and a large enough liquid-solid interface, it is particularly important that the solid support provides a gaseous phase distributed evenly throughout the bioreactor, the volume of which is 20% to 60% of the volume of the bioreactor. Equally important is the continuous fluid-filled capillary pore volume in the material, despite (of) high gas space. The liquid phase is at least 20% of the reactor volume. The greater the gaseous phase, the longer the reaction time and, thus, the more efficient the bioreactor.

Since the requirement is unsaturated state and at the same time a large gas space, the reactor is designed so that there is water saturated small and medium-sized pores in which microbes are able to attach and fit.

In the bioreactor of the invention a suitable gas-liquid state is achieved either by gravitation or by causing the suction in liquid phase or by a combination of both by a porous plate or by overpressure and with a porous plate.

The solid phase comprises a porous solid support in order to obtain sufficient fermentation conditions. The intra pores of solid support particles are preferably within the range of nanometers and micrometers scale. Liquid binds to the pores of the solid support by capillary forces resulting from adsorption and surface tension. Intensity of the binding may be expressed by pressure units, such as Pascals or Bars. A given pore size corresponds to a certain binding intensity.

Assuming that the pores are cylindrical tubes, the radius of the largest pores filled with liquid may be calculated from the following equation (1):

$$r = 2\gamma/\Delta P$$

where r is the radius of the pore (m);
$\gamma$ is the surface tension of liquid, N/m;
$\Delta P$ is the pressure difference between the gas and liquid phase at the gas-liquid surface, $N/m^2$ The solid support suitable for use in the present invention should be such that at least 20% of the pore volumes have pore diameters resulting in a liquid suction of about 0.01 to about 0.1 bar if pores between these sizes are filled with liquid. This is equivalent to pore size of about 300 μm to about 30 μm. It is preferable that the liquid-gas interface in the bioreactor is as large as possible. The smaller the pores are that contain the liquid-gas interfacial area, the greater is the sum of the interfacial area. This provides preferable conditions wherein the capillary conductivity is good (shown in Table 1).

In some embodiments, the solid support comprises or is in the form of particles having a diameter of 0.1 mm to 5 mm for at least 50% of the particles. Any particle size within this range or any combination thereof may be used in the present bioreactor and the related process. This particle size provides in unsaturated conditions a high liquid-gas interface area and a good capillary conductivity of liquids at the same time.

Suitable particle materials include, but are not limited to, material mixtures comprising vermiculite, modified vermiculites, vermiculite-like materials, or synthetic vermiculites; synthetic cation-exchange resins; various peat types; other organic materials; and mixtures thereof as long as they have or they provide the required physical and chemical characteristics described herein.

In one embodiment solid support comprises a mixture of vermiculite (40-60 vol %, 2-4 mm), perlite (20 vol %, 1-2 mm) and synthetic cation exchange resin (20-40 vol %, 0.7 mm).

In some other embodiments the solid support comprises or is in the form of a spongy structure having a pore size distribution within the range of about 0.1 mm to about 5 mm for at least 20% of its pore volumes. Non-limiting examples of suitable spongy materials include synthetic spongy materials, such as foamed plastic polymers, as well as natural sponges.

Still in some other embodiments, the solid support is provided as a filamentous structure. In such cases, inter-filamentous spaces may be regarded as the pores of the filamentous solid support, and their diameter distribution should lie within the range of about 0.1 mm to about 5 mm for at least 20% of the inter-filamentous spaces. A non-limiting example of a suitable filamentous material includes steel wool. As steel wool does not have any cation-exchange properties it may be provided in a mixture with particles having sufficient cation-exchange properties. Alternatively or in addition, steel wool may be coated or applied with an organic material, such as polyacrylamide, in order to achieve sufficient cation-exchange properties.

The porous solid support may also be any admixture of particles, spongy materials and filaments as long as it fulfils the physical requirements set forth herein.

The solid support is inoculated with micro-organisms. The preferable micro-organisms include but are not limited to Acetogenic organisms that are known to synthesise metabolic end-products that can be used as liquid transportation fuels. Acetogenic organisms typically used in commercial syngas fermentation are for example *Moorella thermoacetica, Acetobacterium woodii, Clostridium aceticum Clostridium autoethanogenum, Clostridium jungdahlii,*

*Clostridium ragsdalei* and *Alkalibaculum bacchi*. Fermentation products of these organisms comprise acetate, ethanol, butyrate, butanol and 2,3-butanediol. Ethanol and butanol are used as liquid transportation fuels, while acetate and 2,3-butanediol are of interest in the chemical industry. All acetogens produce acetate, the typically used organisms for specific acetate production are *M. thermoacetica, A. woodii*, and *C. aceticum*. Those primarily used for the production of ethanol include *C. jungdahlii, C. autoethanogenum, C. ragsdalei* and *A. bacchi*. Butanol may be produced by *Clostridium carboxidivorans* and *Butyribacterium methylotrophicum*, while *Clostridium drakei* and *Clostridium scatologenes* are known to produce butyrate. In addition, 2,3-butanediol may be produced by *C. ljungdahlii, C. autoethanogenum* and *C. ragsdalei*. Methane and ammonia-oxidizing bacteria can be employed to partially oxidize methane to methanol. The preferable micro-organisms include but are not limited to ammonia-oxidizing bacteria (AMO) such as *Nitrosomonas europaea* and *Nitrosococcus oceani*. Also mixed nitrifying enrichment cultures can be used for methane-to-methanol conversion.

The micro-organisms may be used in any desired mixture or combination, or as a pure culture of a single species. Also genetically engineered species can be used. The micro-organisms are chosen according to the desired end product. As one specific example, micro-organisms can be used in single-cell protein (SCP) production. In such a case, the naturally occurring methanotroph *Methylococcus capsulatus* may be used in production of bacterial protein from methane.

The micro-organisms may be obtained from culture collections or isolated, for instance, from swamps, such as peat bogs or sphagnum bogs, or other wetlands. The choice of the organism in the present bioreactor may also depend on various factors of the fermentation process including, but not limited to, nutrient, temperature, and pH requirements of a given organism as readily understood by a skilled person.

The porosity of the solid support not only affects the moisture conditions in the bioreactor but also provides a large attachment surface for micro-organisms and protects them from flushing. In addition, porosity increases the specific surface area of the solid support. In some embodiments, the specific surface area of the solid support is at least 5 m$^2$/g.

Besides a high specific surface area the solid support should have a high cationic exchange capacity, typically higher than 0.1 mmol/g. Based on the experience, with the reactor structure presented in example 2, the cationic exchange capacity of the presented reactor structure provides nutrients for the microorganism at least for couple of weeks period without external additions.

Since most nutrient substances are cationic, cation-exchange properties of the solid support are more important than anion-exchange properties. It is however advantageous that the solid support possesses also anion-exchange properties, typically higher than 0.01 mmol/g. This value provides enough anions binding capacity and ensures that the osmotic value in a solution do not rise on a too high level.

In some embodiments, the cation-exchange capacity and the anion-exchange capacity may even be almost equal to each other. The ion-exchange capacity together with the high specific area enables the filling material store available nutrients for microbes. Furthermore, the large specific surface area together with high ion exchange capacity results in formation of a biofilm. This, in turn, increases the efficiency of the fermentation process due to high micro-organism content.

The above-mentioned properties of the solid support provide sufficient buffering properties in the fermentation process. When the solid support, owing to its ion-exchange capacity, is capable of exchanging hydrogen and/or hydroxyl ions with a liquid phase, there should be no need for additional pH controlling.

The ion-exchange capacity, high specific surface area and the appropriate pore size distribution make the filling material of the solid state reactor active. The continuous liquid circulation for maintaining the appropriate nutrient concentrations and pH-value is not needed thus making the microbial processing in unsaturated filling material conditions possible.

Solid supports not suitable for use in the present invention include materials that are inactive in terms of their ion-exchange capacity. More specific examples of such materials include silica-based materials, wood-based materials, most plastics (unless they are coupled with active groups), and most stone materials, such as feldspar and quartz. It is noteworthy that although vermiculite exists in forms having a sufficient cation exchange capacity, it is not a suitable solid support material to be used alone in the present bioreactor. This is because it is not possible to achieve a sufficient gaseous phase volume with sole vermiculite. Spontaneous compaction through wetting and drying effect would reduce the gaseous phase volume below 20% of the volume of the bioreactor even if in some specific cases it might be possible to achieve an initial gaseous phase volume of slightly over 20% of the volume of the bioreactor. Another outcome of the compaction is the possible reduction of the capillary conductivity. Thus, if vermiculite is to be employed in the present bioreactor, it needs to be provided in a mixture with other, non-flat materials, such as perlite, in order to fulfil the requirement that the volume of the gaseous phase must be 20% to 60% of the volume of the bioreactor and in order to increase the capillary conductivity.

Capillary conductivity and sufficient inter-solid-support gas volume define the gas and liquid flow characteristics through the solid support. In reactions which generate liquid products or liquid is a starting material, capillary conductivity is very important. Adequate capillary conductivity is required to ensure that the gas and liquid transfer can be maintained at the desired levels for the duration of the fermentation process. Too high moisture content decreases gas volume in the reactor thus reducing the reaction time and the gas-liquid interface area.

Capillary conductivity is needed in the bioreactor in order to avoid the largest pores to be filled with the liquid and is needed for the liquid product flow out of the reactor in the capillary pores in unsaturated conditions. In the present invention adequate unsaturated capillary conductivity is greater than 0.1 cm/h, wherein the time unit is hour (h), the length unit is centimeter (cm), volume unit is cm$^3$, the unit of velocity is cm/h, and the pressure unit is defined as the liquid column height in cm.

Capillary conductivity greater than 0.1 cm/h is needed/demanded because as shown in table 1, if the bioreaction produces more water than is the water conductivity of the solid support, the bottom of the bioreactor gets waterlogged/gets saturated with water and leads poor reactor efficiency (productivity/power).

Capillary conductivity may be calculated from the following equation (2):

$$q = KH/L$$

q=flow rate (cm/h)
K=hydraulic conductivity coefficient (cm/h)

H=the potential difference expressed as the height of the liquid column (cm)

L=the length of the flow path (cm)

The bioreactor of the invention may be made, for instance of glass, stainless steel, or it may be, for instance, a plastic tank or vessel. The material of the bioreactor should be non-toxic to the used in the process. The size and shape of the bioreactor may vary within a range known to a person skilled in the art depending on different parameters, such as the choice of the solid support material. Preferably, the size is suitable for industrial scale production. The bioreactor should be low-cost, easy to operate, and reliable.

Figure 1:
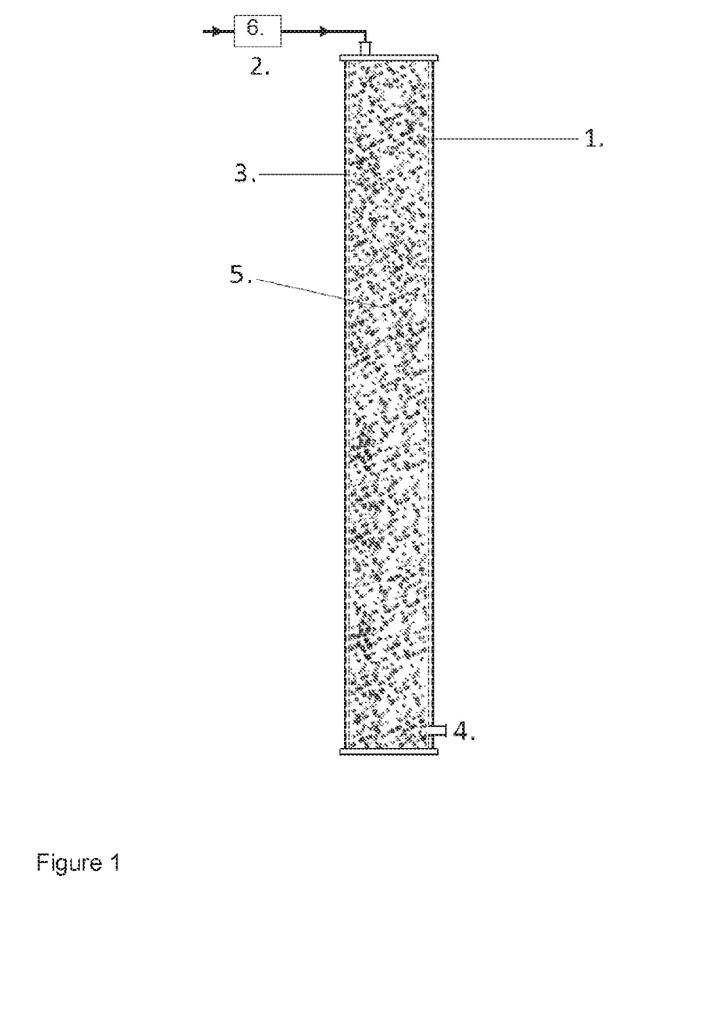
FIG. 1 shows a schematic representation of an exemplary bioreactor, in which suction and unsaturated state is achieved by gravitation. When unsaturated capillary conductivity is high enough, the reactor is not saturated with water (liquid), if e.g. the reaction produces water (liquid).

An exemplary bioreactor according to the invention is illustrated in FIG. 1. The upper end of the bioreactor vessel (1) is provided with a gas distribution system (2) and with mass flow controller (MFC) (6) whereas the lower end of the vessel (1) is provided with a possible gas, liquid and/or solid collection system (4). The reactor vessel is loaded with a porous solid support material (5) described herein. The bioreactor vessel is surrounded by a heating water circulation (3).

Figure 2:
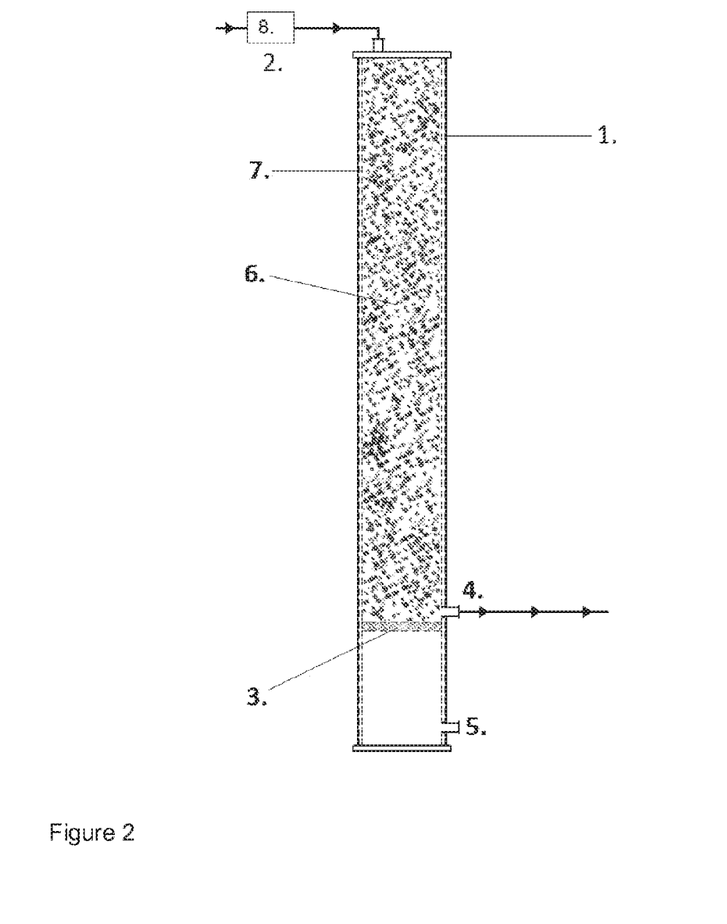
FIG. 2 shows a schematic representation of an exemplary bioreactor, in which suction and unsaturated state is achieved by gravitation and the influence of gravitation is intensified by suction caused by a porous plate. In order to be successful, intensification requires a good capillary conductivity in an unsaturated state.

Another exemplary of a bioreactor is shown in FIG. 2. In this bioreactor gas supply is adjusted with mass flow controllers and pressure regulators. The upper end of the bioreactor vessel (1) is provided with a gas distribution system (2) and with mass flow controller (MFC) (8) whereas the lower end of the vessel (1) is provided with a possible gas collection system (4). A porous ceramic plate is placed on the bottom of the reactor vessel (3) above the liquid collection system and a suction system (5). The reactor vessel is loaded with a porous solid support material (6) described herein. The bioreactor vessel is surrounded by a heating water circulation (7).

Figure 3:
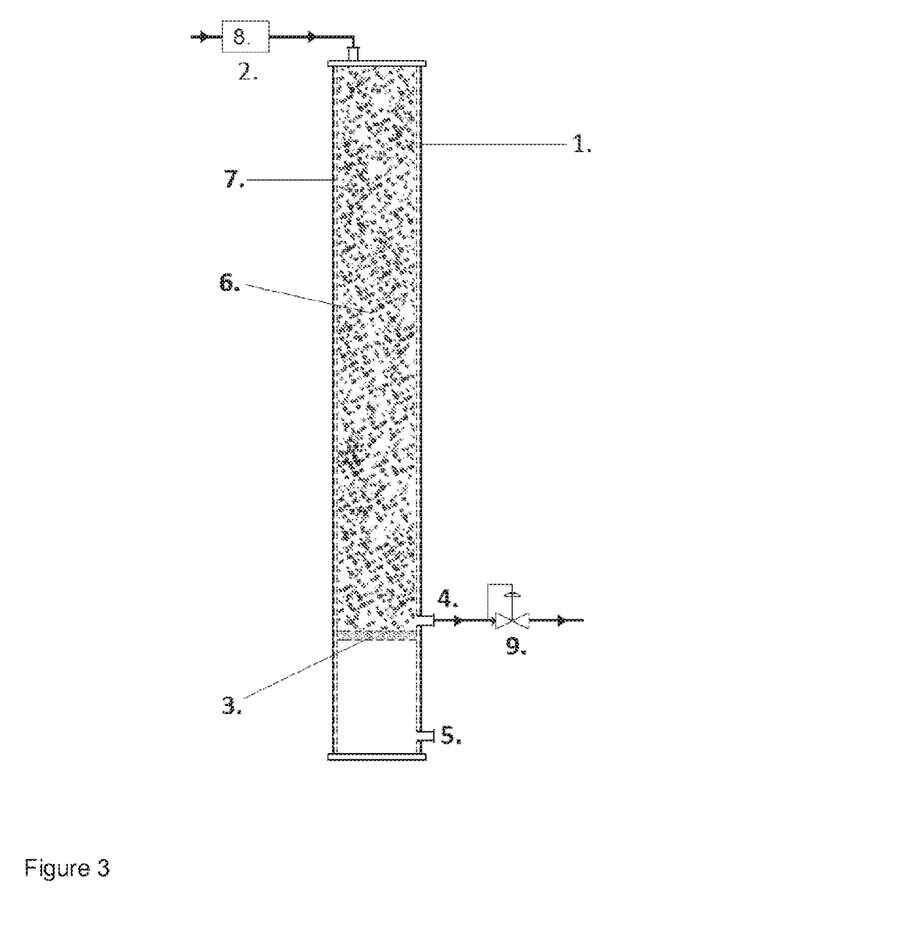
FIG. 3 shows a schematic representation of an exemplary bioreactor, in which suction and unsaturated state is achieved by gravitation and the influence of gravitation is intensified by suction caused by a porous plate and over pressure.

Still another exemplary of a bioreactor is shown in FIG. 3. In this bioreactor gas supply is adjusted with mass flow controllers and pressure regulators. The upper end of the bioreactor vessel (1) is provided with a gas distribution system (2) and with mass flow controller (MFC) (8) whereas the lower end of the vessel (1) is provided with a possible gas collection system (4) with a gas pressure regulator (9). A porous ceramic plate is placed on the bottom of the reactor vessel (3) above the liquid collection system (5). The reactor vessel is loaded with a porous solid support material (6) described herein. The bioreactor vessel is surrounded by a heating water circulation (7).

Although the active filling material does not require adjusting the bioreactor parameters, the bioreactor may be provided with various sensors for monitoring desired parameters such as the temperature, pH, and humidity in the reactor. Such sensors are readily available in the art. The bioreactor may also be provided with an analyser for monitoring the operation of the bioreactor and the yield of liquid.

Temperature control of the bioreactor may be obtained e.g. by connecting a closed water circulation system to the bioreactor. Such a system may provide either heating or cooling of the fermentation process depending on the needs of a given micro-organism. Heat is transferred between the water circulation system and the bioreactor by conductivity. Other means and methods for adjusting the temperature of the present process are well known in the art.

The present invention relates further to a process for liquid products from gases or gases and liquids by solid state fermentation. The process comprises the steps of a) providing a bioreactor according to the invention;

b) feeding gas(es) or gas(es) and liquid(s) into the reactor, c) anaerobically or aerobically bioconverting the starting materials into gas, liquid and/or solid products, and d) collecting the producs from the bioreactor.

Desired gas or liquid source used as a starting material in the fermentation process of the invention may be captured from any suitable source including, but not limited to syngas produced/generated from gasification of carbonaceous feedstocks.

The fermentation process is carried out under conventional conditions used for culturing desired micro-organisms, i.e. using aerobic or anaerobic conditions.

Micro-organisms require nutrients for their growth. These substances may be attached to a solid support having cation-exchange capacity and anion-exchange capacity as described above thus resulting in a self-sustained process in this respect. Nitrogen may be given e.g. in the form of urea or ammonium carbonate. The specific concentration on these elements depends on the micro-organism being used.

By binding the nutrients on cation and anion exchangers they can be stored for a later use without ion concentration (osmosis value) rising too high in a liquid solution. In this way also a self-sustained system is achieved with respect to pH. Thus, no buffer solutions are needed in order to keep pH at a nearly constant value.

Furthermore, self-sustainability concerns also the gas and liquid state of the system. With a suitable pore size of the particles the desired gas and liquid volumes and also capillary conductivity is achieved in the reactor structure.

Additional nutrients may be supplied during the fermentation process.

A functional bioreactor and solid state fermentation process according to the present invention may be set up in a short period of time, such as a couple of days.

Example 1

The preferable conditions for a porous solid support were tested with a mixture comprising vermiculite, perlite and cation exchange resins.

TABLE 1

Physical properties of the solid support from a mixture of vermiculite (40 vol %, 2-4 mm), synthetic cation exchange resins (40 vol %, 0.7 mm) and perlite (20 vol %, 1-2 mm).

| Suction expressed in the height of a water column (in cm or bars) | | Suction corresponding pore radius, | Air space $cm^3/cm^3$ (of the total | Liquid-gas interface | Water conductivity, |
|---|---|---|---|---|---|
| cm | bar | cm | volume) | $cm^2/cm^3$ | cm/h |
| 0 | 0 | — | 0 | 0 | 1.69 |
| 10 | 0.01 | 0.03 | 0.099 | 6.6 | 1.41 |
| 20 | 0.02 | 0.015 | 0.249 | 36.6 | 0.24 |
| 30 | 0.03 | 0.01 | 0.283 | 47.9 | 0.028 |
| 40 | 0.04 | 0.0075 | 0.295 | 53.5 | 0.0085 |
| 50 | 0.05 | 0.0060 | 0.295 | 53.5 | 0.0085 |

Table 1 shows that the largest pores do not produce a large liquid-gas interface. Excessive particle size reduction quickly produces low water conductivity. Size of the pores between the particles is between to % of the size of the particles.

If bioreactor produces methane from hydrogen and carbon dioxide at 10 W/l efficiency (power) according to the Sabatier equation $CO_2 + 4H_2 \rightarrow CH_4 + 2H_2O$ water is produced at rate 1.35 g/h/l. This means that near a bottom of a one meter high bioreactor structure downward flow of water is 0.135 cm/h.

Water conductivity values in Table 1 indicate that the suction cannot increase near the bottom of the bioreactor value 0.03 bar. This results in poor reactor efficiency (power) near the bottom of the reactor (the residence time is not a maximum, the liquid-gas interface is not a maximum) near the bottom of the base.

This problem will get worse with increasing reactor efficiency (power) or with increasing height of the reactor.

Example 2

Figure 4:
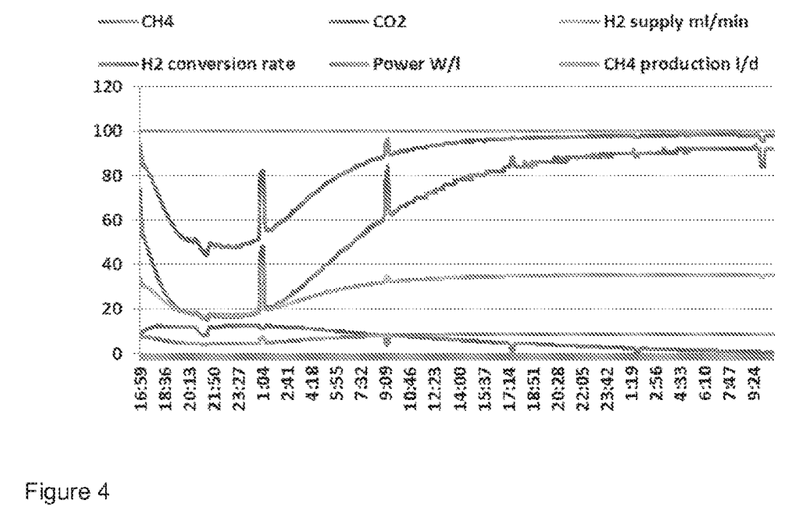

This Example shows a liquid product exiting the solid state fermentation reactor by gravitation.

Bioreactor is constructed as illustrated in FIG. 1 from a polypropylene sewer pipe (inner diameter of 75 mm, height of 500 mm, working volume of 2 L). A nylon inlet tube for gas is fitted to the upper part of the pipe. Gas supply is adjusted with mass flow controllers. The bioreactor is provided with an outlet tube fitted to the lower part of the pipe for gas and liquid end product collection.

The upper part of the sewer pipe of the bioreactor is filled with a solid support. Prior to the filling, solid support is produced by mixing 6 l 2-4 mm vermiculite with 2 l 2-5 mm perlite and 2 l cation exchange resins. In addition, N and P source, supplemented with other minerals are added in this mixture to serve as a nutrient and trace element source for the bioreaction. The bioreactor is inoculated with micro-organisms ammonia-oxidizing bacteria (AMO) such as *Nitrosomonas europaea* and *Nitrosococcus oceani*. The temperature of the bioreactor is adjusted by a water jacket on a level desired by the used micro-organism(s). Microbial culture medium recirculation is possible with outlet liquid from the collector tank of the bioreactor.

Removal of the end product is efficiently achieved as a result of the good capillary conductivity of the reactor for a mixture of methanol and water. In the end product, methanol is dissolved in water and the good capillary water conductivity of the reactor contributes to the removal of the product from the reactor. The good water capillary conductivity of the reactor means that capillary conductivity is also good for a mixture of water and methanol. Efficient product removal from a bioreactor is important and will likely intensify the production since methane oxidation to methanol is known to be inhibited by the product itself ($CH_3OH$).

Example 3

This Example shows a solid product (cell biomass) exiting the solid state fermentation reactor by gravitation. Specifically, in this example microbial protein is produced from methane using biological conversion in a solid state fermentation reactor.

Bioreactor is constructed as illustrated in FIG. 1 from a polypropylene sewer pipe (inner diameter of 75 mm, height of 500 mm, working volume of 2 L). A nylon inlet tube for gas is fitted to the upper part of the pipe. Gas supply mixture of methane and oxygen is adjusted with mass flow controllers. The bioreactor is provided with an outlet tube fitted to the lower part of the pipe for gas, liquid and solid end product (single cell protein biomass) collection.

The upper part of the sewer pipe of the bioreactor is filled with a solid support. Prior to the filling, solid support is produced by mixing 6 l 2-4 mm vermiculite with 2 l 2-5 mm perlite and 2 l cation exchange resins. In addition, N and P source supplemented with other minerals are added in this mixture to serve as a nutrient and trace element source for the bioreaction. The bioreactor is inoculated with methano-trophs such as *Methylococcus capsulatus*. The temperature of the bioreactor is adjusted by a water jacket on a level desired by the used micro-organism(s). Microbial culture medium recirculation is possible with outlet liquid from the collector tank of the bioreactor.

Optimal operation of the bioreactor requires the removal of microbial biomass from the reactor. In an effective capillary suction area, the capillary pore size is such that the microbes fit well to move with water out of the reactor and will be removed with water from a reactor.

What is claimed is:

1. A bioreactor comprising:
   (1) a gas or gas and liquid distribution system; and
   (2) a gas or liquid or solids collection system, wherein the bioreactor comprises a solid phase, a liquid phase and a gaseous phase, the solid phase comprises a porous solid support in which at least 20% of the pore volumes have a pore size resulting in a liquid suction of about 0.01 to about 0.1 bar if pores of this sizes are filled with liquid, the porous solid support is inoculated with desired micro-organisms, the unsaturated capillary conductivity of the packed solid material is at least 0.1 cm/h, said solid support has a cationic exchange capacity of at least 0.1 mmol/g, anion exchange capacity of at least 0.01 mmol/g, and a specific surface area of at least 5 $m^2/g$, the volume of the gaseous phase is 20% to 60% of the volume of the bioreactor, the liquid phase is at least 20% of the reactor volume and the solid support material is not silica-based material.

2. The bioreactor according to claim 1, further comprising (3) a collection system for a combination of gas, liquid and solids.

3. The bioreactor according to claim 1, wherein said porous solid support comprises particles having a diameter of 0.1 mm to 5 mm for at least 50% of the particles.

4. The bioreactor according to claim 1, wherein said porous solid support comprises a spongy material having a pore size of 0.1 mm to 5 mm for at least 20% of its pores.

5. The bioreactor according to claim 4, wherein said spongy material is selected from the group consisting of synthetic spongy materials and natural sponges.

6. The bioreactor according to claim 1, wherein said porous solid support comprises a filamentous material, wherein the diameter of inter-filamentous spaces is from 0.1 mm to 5 mm for at least 20% of its inter-filamentous spaces; or a mixture thereof.

7. The bioreactor according to claim 6, wherein said filamentous material is coated or non-coated steel wool.

8. A process generating from gases or gases and liquids by solid state fermentation, the process comprising:
   a) providing a bioreactor, the bioreactor comprising:
   (1) a gas or gas and liquid distribution system; and
   (2) a gas or liquid or solids collection system, wherein the bioreactor comprises a solid phase, a liquid phase and a gaseous phase, the solid phase comprises a porous solid support in which at least 20% of the pore volumes have a pore size resulting in a liquid suction of about 0.01 to about 0.1 bar if pores of this sizes are filled with liquid, the porous solid support is inoculated with desired micro-organisms, the unsaturated capillary conductivity of the packed solid material is at least 0.1 cm/h, said solid support has a cationic exchange capacity of at least 0.1 mmol/g, anion exchange capacity of at least 0.01 mmol/g, and a specific surface area of at least 5 $m^2/g$, the volume of the gaseous phase is 20% to 60% of the volume of the bioreactor and the liquid phase is at least 20% of the reactor volume and the solid support material is not silica-based material;

b) feeding gas or gases and liquids into the bioreactor;

c) bioconverting anaerobically or aerobically said gas or gases and liquids into gaseous, liquid or solid products; and d) collecting the product from the bioreactor. comprising vermiculite-like material, material mixtures comprising synthetic vermiculites, synthetic cation exchange resins, various peat types, and mixtures thereof.

9. The process according to claim 8, wherein said porous solid support comprises particles having a diameter of 0.1 mm to 5 mm for at least 50% of the particles.

10. The process according to claim 8, wherein said porous solid support comprises a spongy material having a pore size of 0.1 mm to 5 mm for at least 20% of its pores.

11. The process according to claim 10, wherein said spongy material is selected from the group consisting of synthetic spongy materials and natural sponges.

12. The process according to claim 8, wherein said porous solid support comprises a filamentous material, wherein the diameter of inter-filamentous spaces is from 0.1 mm to 5 mm for at least 20% of its inter-filamentous spaces; or a mixture thereof.

13. The process according to claim 12, wherein said filamentous material is coated or non-coated steel wool.

14. The process according to claim 8, wherein the bioreactor further comprises (3) a collection system for a combination of gas, liquid and solids.

* * * * *